(12) United States Patent
Neri et al.

(10) Patent No.: US 8,796,426 B2
(45) Date of Patent: Aug. 5, 2014

(54) COMBINATION OF AN ANTI-EDB FIBRONECTIN ANTIBODY-IL-2 FUSION PROTEIN, AND A MOLECULE BINDING TO B CELLS, B CELL PROGENITORS AND/OR THEIR CANCEROUS COUNTERPART

(75) Inventors: Dario Neri, Zurich (CH); Hans Dietrich Menssen, Berlin (DE); Andreas Menrad, Cambridgeshire (GB); Christoph Schliemann, Zurich (CH)

(73) Assignee: Philogen S.p.A., Sienna (IT)

( * ) Notice: Subject to any disclaimer, the term of this patent is extended or adjusted under 35 U.S.C. 154(b) by 591 days.

(21) Appl. No.: 12/270,174

(22) Filed: Nov. 13, 2008

(65) Prior Publication Data

US 2009/0202473 A1 Aug. 13, 2009

Related U.S. Application Data

(60) Provisional application No. 61/021,718, filed on Jan. 17, 2008.

(30) Foreign Application Priority Data

Jan. 17, 2008 (EP) .................................. 08075044

(51) Int. Cl.
  C07K 16/30 (2006.01)
  C07K 14/55 (2006.01)
  C07K 16/46 (2006.01)
  A61P 35/00 (2006.01)
  A61P 37/06 (2006.01)

(52) U.S. Cl.
  USPC ................... 530/387.7; 435/69.52; 435/69.7; 514/16.6; 514/19.3; 514/814; 530/868; 424/810

(58) Field of Classification Search
  None
  See application file for complete search history.

(56) References Cited

U.S. PATENT DOCUMENTS

2004/0013640 A1* 1/2004 Zardi et al. ................... 424/85.1
2006/0251617 A1* 11/2006 Denis-Mize et al. ........ 424/85.2

FOREIGN PATENT DOCUMENTS

| EP | 1842553 A1 | 10/2007 |
| EP | 08075044 R | 6/2008 |
| WO | 0162298 A2 | 8/2001 |
| WO | 03049694 A2 | 6/2003 |
| WO | 2006089064 A1 | 8/2006 |
| WO | PCTEP2008009441 R | 5/2009 |

OTHER PUBLICATIONS

Habermann, 2007. Hematology, pp. 257-226.*
Schliemann et al (2009. Blood. 113(10): 2275-2283).*
Mavromatis et al, 2003. J Clin Oncol. 21: 1874-1881.*
Pini et al., 1998. J Biol Chem. 273:21769-21776.*
Sauer et al (Nov. 16, 2006. Blood 108(11):156B).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*

(Continued)

Primary Examiner — Zachary Howard
(74) Attorney, Agent, or Firm — Millen, White, Zelano & Branigan, P.C.

(57) ABSTRACT

The present invention relates to a combination of an anti-EDb fibronectin antibody-IL-2 fusion protein, and a molecule binding to B cells, B cell progenitors and/or their cancerous counterpart and uses thereof.

18 Claims, 5 Drawing Sheets

(56) References Cited

OTHER PUBLICATIONS

Figure 1:
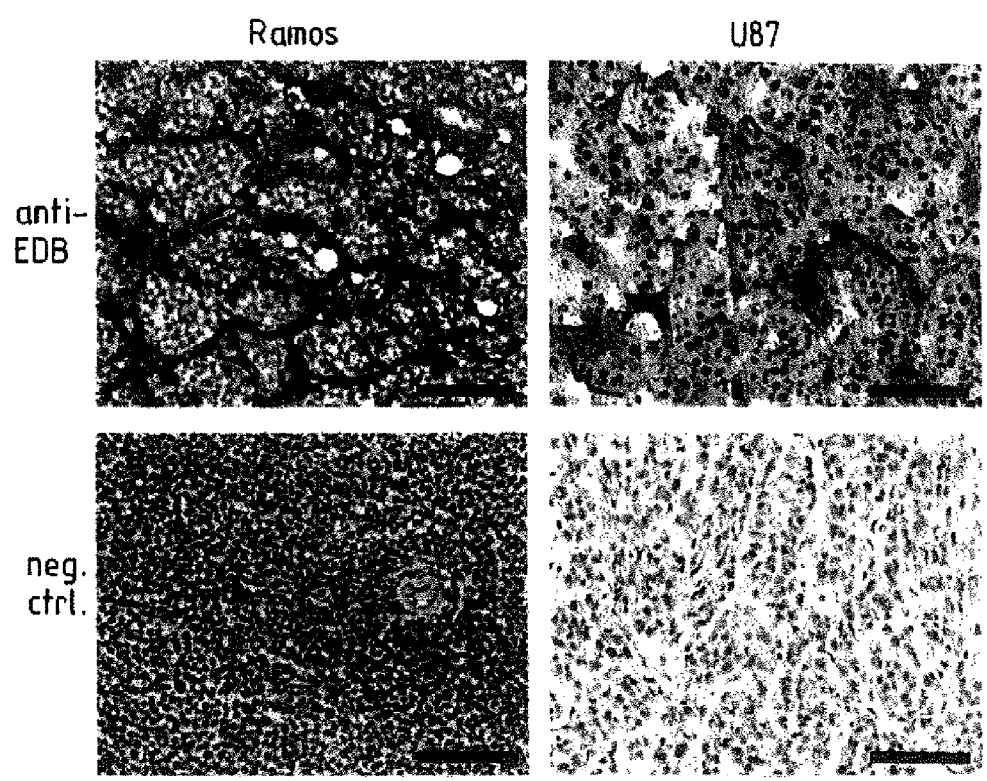

Skolnick et al (2000) Trends in Biotech. 18(1): 34.*
Doerks et al (1998) Trends in Genetics 14(6): 248.*
Brenner (1999) Trends in Genetics 15(4): 132.*
Rudikoff et al (1982. Proc Natl Acad Sci USA. 79: 1979-1983).*
MacCallum et al (1996. Journal of Molecular Biology. 262: 732-745).*
Pascalis et al (2002. Journal of Immunology. 169:3076-3084).*
Casset et al (2003. Biochemical and Biophysical Research Communications. 307: 198-205).*
Vajdos et al (2002. Journal of Molecular biology. 320: 415-428).*
Holm et al (2007. Molecular Immunology. 44: 1075-1084).*
Chen et al (1999. Journal of Molecular Biology. 293: 865-881).*
Wu et al (1999. Journal of Molecular Biology. 294: 151-162).*

* cited by examiner

A

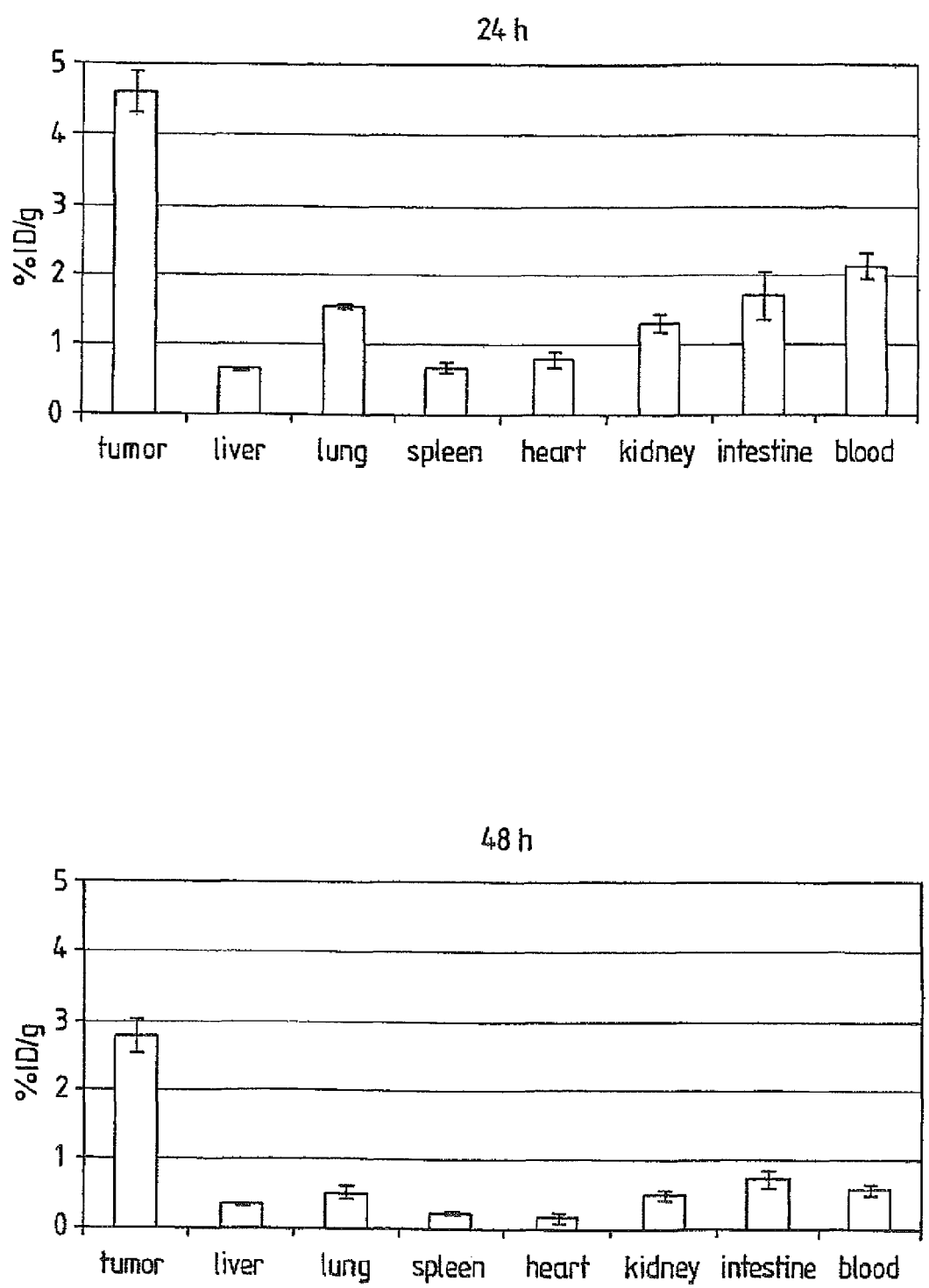

Diffuse large
B-cell lymphoma

Diffuse large
B-cell lymphoma

Burkitt
lymphoma

SEQUENCE LISTING

<160> NUMBER OF SEQ ID NOS: 11

<210> SEQ ID NO 1

<211> LENGTH: 116
<212> TYPE: PRT
<213> ORGANISM: Artificial Sequence
<220> FEATURE:
<223> OTHER INFORMATION: Vh L19

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser
            115

<210> SEQ ID NO 2
<211> LENGTH: 108
<212> TYPE: PRT
<213> ORGANISM: Artificial Sequence
<220> FEATURE:
<223> OTHER INFORMATION: Vl L19

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 3
<211> LENGTH: 12
<212> TYPE: PRT
<213> ORGANISM: Artificial Sequence
<220> FEATURE:
<223> OTHER INFORMATION: Linker

<400> SEQUENCE: 3

Gly Asp Gly Ser Ser Gly Gly Ser Gly Gly Ala Ser
1               5                   10

<210> SEQ ID NO 4
<211> LENGTH: 133

```
<212> TYPE: PRT
<213> ORGANISM: Homo sapiens

<400> SEQUENCE: 4

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 5
<211> LENGTH: 17
<212> TYPE: PRT
<213> ORGANISM: Artificial Sequence
<220> FEATURE:
<223> OTHER INFORMATION: Fusion protein linker

<400> SEQUENCE: 5

Glu Phe Ser Ser Ser Ser Gly Ser Ser Ser Gly Ser Ser Ser
1               5                   10                  15

Gly

<210> SEQ ID NO 6
<211> LENGTH: 5
<212> TYPE: PRT
<213> ORGANISM: Artificial Sequence
<220> FEATURE:
<223> OTHER INFORMATION: CDR1 Vh

<400> SEQUENCE: 6

Ser Phe Ser Met Ser
1               5

<210> SEQ ID NO 7
<211> LENGTH: 7
<212> TYPE: PRT
<213> ORGANISM: Artificial Sequence
<220> FEATURE:
<223> OTHER INFORMATION: CDR3 Vh

<400> SEQUENCE: 7

Pro Phe Pro Tyr Phe Asp Tyr
1               5

<210> SEQ ID NO 8
<211> LENGTH: 17
<212> TYPE: PRT
<213> ORGANISM: Artificial Sequence
<220> FEATURE:
```

```
<223> OTHER INFORMATION: CDR2 Vh

<400> SEQUENCE: 8

Ser Ile Ser Gly Ser Ser Gly Thr Thr Tyr Tyr Ala Asp Ser Val Lys
1               5                   10                  15
Gly

<210> SEQ ID NO 9
<211> LENGTH: 12
<212> TYPE: PRT
<213> ORGANISM: Artificial Sequence
<220> FEATURE:
<223> OTHER INFORMATION: CDR1 Vl

<400> SEQUENCE: 9

Arg Ala Ser Gln Ser Val Ser Ser Ser Phe Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: CDR2 Vl

<400> SEQUENCE: 10

Tyr Ala Ser Ser Arg Ala Thr
1               5

<210> SEQ ID NO 11
<211> LENGTH: 9
<212> TYPE: PRT
<213> ORGANISM: Artificial Sequence
<220> FEATURE:
<223> OTHER INFORMATION: CDR3 Vl

<400> SEQUENCE: 11

Gln Gln Thr Gly Arg Ile Pro Pro Thr
1               5
```

COMBINATION OF AN ANTI-EDB FIBRONECTIN ANTIBODY-IL-2 FUSION PROTEIN, AND A MOLECULE BINDING TO B CELLS, B CELL PROGENITORS AND/OR THEIR CANCEROUS COUNTERPART

This application claims the benefit of the filing dates of U.S. Provisional Application Ser. No. 61/021,718 filed Jan. 17, 2008, and EP application 08075044.1, filed Jan. 17, 2008, which are incorporated by reference herein.

The present invention relates to a combination of an anti-EDb fibronectin antibody-IL-2 fusion protein, and a molecule binding to B cells, B cell progenitors and/or their cancerous counterpart and uses thereof.

B cell non-Hodgkin lymphoma (B-NHL), a group of histopathologically and clinically distinct malignancies derived from B lymphocyte precursor cells, is the most common group of hematologic malignancies. Accordingly, malignant lymphocytes from B-NHL patients express characteristic B cell markers on their cell surfaces such as CD20, CD 23 and others. B-NHL accounts for over 50000 newly diagnosed cases and 5% of cancer-related deaths in the United States each year.

Rituximab (RITUXAN®) is a chimeric monoclonal IgG1 antibody that directly binds to the CD20 cell surface epitope constitutively expressed on the cell surface of malignant and normal B cell populations. By so doing, rituximab (a) elicits antibody-dependent cellular cytotoxicity (ADCC), (b) induces lymphoma cell death through complement-dependent cytolysis (CDC) and/or complement-dependent cellular cytotoxicity, and (c) directly induces apoptosis following the engagement of CD20 by rituximab. In addition, (d) rituximab possibly has a vaccinal effect implemented via cross-presentation of lymphoma antigens from rituximab-killed malignant B cells by antigen-presenting cells and priming of lymphoma antigen-specific cytotoxic T cells (Selenko et al, 2001).

A) ADCC: This mechanism involves binding of the antibody's Fc portion to the Fcγ receptors expressed on immune cells with cytotoxic capabilities such as monocytes, natural killer cells, and granulocytes, which would then lead to destruction of the rituximab-bound B cells either by phagocytosis or release of cytotoxic granules contained in immune effector cells. ADCC is currently considered to be the major mechanism of action of rituximab.

B) CDC: Since the Fc portion of rituximab binds to complement, lymphoma cell death can be achieved through CDC. However, recent findings that rituximab-induced B cell depletion still occurs in mice genetically deficient of complement factors tempered the initial enthusiasm for this mechanism of action.

C) Induction of apoptosis: In vitro studies have shown that engagement of CD20 by rituximab triggers a cascade of intracellular signaling events and selective down-regulation of antiapoptotic factors. It also translocates CD20 into lipid rafts and activates caspase via increased calcium mobilization (Janas et al, 2005). In CLL patients, it was found that circulating B cells display activation of several caspases and poly (ADP-ribose) polymerase (PARP) cleavage immediately after the infusion of rituximab, long before other potential mechanisms such as ADCC could be triggered in vivo (Byrd et al, 2002).

D) Vaccinal effect/T cell response: The clinical findings that retreatment with rituximab was associated with a longer median response duration as the first treatment was and that in those patients who responded to retreatment, the antitumor effect of rituximab persisted long after the antibody was cleared from the circulation (Davis et al, 2000) strongly hints to a specific immunologic mechanism involved.

Treatment with rituximab as a single agent induces significant but moderate and short-lasting responses in patients with almost every subtype of B-cell lymphoma. However, its biggest benefit is seen when it is combined with induction chemotherapy regimens (Coiffier, 2006). Combined with standard chemotherapy, in particular with CHOP (cyclophosphamide, vincristine, adriamycin and prednisolone), rituximab at a dose of 375 mg/m$^2$ as a 90-min intravenous infusion on day 1 of each chemotherapy cycle even increases the cure rate of patients with diffuse large B cell lymphoma (DLBCL) to approximately 52% (Coiffier 2002, update of GELA OS data, ASH 2007) from 38% with chemotherapy alone.

In indolent lymphoma, the addition of rituximab to every induction chemotherapy combination (FCM, CVP, CHOP, FND) has resulted in a significant increase in the overall response and complete remission rates as well as in a delay of the time to disease progression (Marcus, 2005; Hiddemann 2005). However, adding rituximab to chemotherapy not always leads to improved clinical outcomes. In patients with mantle cell lymphoma, treatment with CHOP plus rituximab resulted in a similar progression-free survival and overall survival compared with patients on CHOP therapy alone (Lenz et al, 2005).

In addition to its established role as a treatment to induce remissions (induction therapy) in B-NHL patients, rituximab monotherapy also has been evaluated as a maintenance therapy to consolidate responses or prolong remissions. Under the assumption that 25 mg rituximab/ml is the lowest acceptable serum concentration, a dose of 375 mg/m$^2$ rituximab infused every 3 months was found to be sufficient for rituximab maintenance therapy in a prospective pharmacokinetic study (Gordan, 2005). Although some studies have shown a significant clinical benefit when using maintenance rituximab after initial standard chemotherapy with CVP (Hoechster, 2005) or CHOP (Habermann, 2006), it is still unclear whether rituximab maintenance therapy provides additional benefit to those patients in whom it was used as a part of the induction chemotherapy (e.g. R-CHOP).

Unfortunately and despite the unquestionable clinical effectiveness of rituximab in combination with chemotherapy (e.g. R-CHOP), the majority of B-NHL patients still dies eventually of progressive disease. In addition, despite being an effective agent in the treatment of B-NHLs, approximately 50% of patients with relapsed/refractory CD20+ follicular lymphomas do not respond to initial treatment with rituximab (innate resistance; McLaughlin et al 1998), and about 60% of prior rituximab responding patients will not benefit from retreatment with rituximab (acquired resistance; Davis et al, 2000). It is currently unclear, whether these forms of rituximab-resistance are due to an adaptive property of the malignant B cells or to an impaired host's immune effector mechanism. Anyway, rituximab resistance represents a significant barrier to immuno- and immonochemotherapy of B-NHLs in terms of further improved clinical outcome.

Although rituximab/chemotherapy combinations have been analyzed, there is still a strong and persistent need for further therapy improvements. Two general strategies are currently being pursued: a) engineering novel anti-CD20 antibodies, and b) creating monoclonal antibodies that target B cell antigens other than CD20. Two categories of new anti-CD20 monoclonal antibodies are currently in clinical evaluation: a) anti-CD20 antibodies displaying higher affinity than rituximab for the Fc-receptor FcγRIIIa (CD16), and b) anti CD20 antibodies with lower immunogenicity (humanized; Tbl 1). The presumably strongest of these antibodies, GA-101, a humanized anti CD20 antibody with a glyco-engineered Fc portion and a modified elbow hinge results in a 10-100 fold increase in ADCC against NHL cell lines. Small phase I/II studies with anti-CD20 antibodies with lower immunogenicity show response rates in the order of 50% in relapsed B-NHL patients (Coiffier, 2006; Hagenbeek, 2005; Morschhauser, 2005). Monoclonal antibodies targeting surface molecules other than CD20 in B-NHLs such as lumiliximab (anti-CD23), epratuzumab (anti-CD22), SGN-40 and HCD122 (both anti-CD40), galiximab (anti-CD80), apolizumab (Hu1D10), KRN848, 1D09C3 (all anti-HLA-DR) have shown promise in early clinical trials. Novel anti-CD20 antibodies and antibodies directed against non-CD20 B-cell epitopes will have to demonstrate a significantly superior efficacy over rituximab to be considered successful, however, early clinical results with the most of these antibodies indicate incremental benefits, only.

There have been efforts to combine rituximab with unconjugated IL-2 (Eisenbeis et al., 2004; Gluck et al., 2004).

However, the results of a recent phase II trial indicated that "rituximab plus rIL-2 combination therapy was safe and generally well tolerated, but responses were low" (Khan et al., 2006, Clin Cancer Res 2006; 12(23): 7046-7053). Also, it was found that "rIL-2 expands FcR-bearing cellular subsets in vivo and enhances in vitro ADCC of rituxumab". However, it was concluded by the authors that these findings "did not directly translate into meaningful clinical benefit for patients with rituxumab-refractory NHL". Moreover, the authors concluded that "a better understanding of rituximab's in vivo a mechanism of action will likely be required before further advances in favorably modulating its antitumor activity can be made".

In addition to cancer indications, anti B cell antibodies an rituximab in particular are being developed for the treatment of autoimmune diseases, including rheumatoid arthritis, Crohn's disease and autoimmune hemolytic anemia. (Assous et al, 2008).

Taking into consideration standard therapies as well as new treatment options currently in clinical development, there is still a strong medical need for designing more active treatments for B-cell lymphoma patients, which preferentially lead to complete remissions and/or are useful to treat rituximab-resistant lymphoma. There is also a strong medical need for providing new medicaments for treating autoimmune disease, in particular chronic autoimmune diseases.

TABLE 1

Anti-CD20 antibodies

| Antibody name | Type | ADCC | CDC (complement-dependent cytotoxicity) | Direct effects | Reference |
|---|---|---|---|---|---|
| rituximab | Chimeric IgG1 | ++ | ++ | + | Cragg et al |
| Ocrelizumab | Humanized IgG1 | +++ | +/− | + | Vugmeyster et al |
| PRO131921 | Engineered ocrelizumab | ++++ | ++ | + | |
| Veltuzumab | Humanized IgG1 | ++ | ++ | + | Stein et al |
| Ofatumumab | Human IgG1 | ++ | ++++ | + | Hagenbeck et al |
| AME-133 | Humanized IgG1 | ++++ | ++ | ++ | Weiner et al |
| GA-101 | Humanized IgG1 | +++++ | − | ++++ | Umana et al |

TABLE 2

Selected anti-B cell antibodies in clinical trials with non-Hodgkin lymphoma patients

| Antibody name | Type | DLT | Objective response rate, (%, NHL entity)/clinical data | Reference |
|---|---|---|---|---|
| Rituximab | Chimeric IgG1 | None | 48, relapsed FL | McLaughlin et al |
| Epratuzumab (anti-CD22) | Humanized IgG1 | None | 43, relapsed FL | Leonard et al (a) |
| Epratuzumab + rituximab | Combination | None | 67, relapsed FL | Leonard et al (b) |
| Lumiliximab (anti-CD23) | | None | Active in CLL when combines w/chemo | |
| Galiximab (anti-CD80) | Humanized IgG1 | None | 11, relapsed FL | Czuczman et al |
| Galiximab + rituximab | Combination | None | 66, relapsed FL | Leonard et al (c) |
| SGN-40, (anti-CD40) | Humanized IgG1 | Cytokine release | 0 | Advani et al |
| HCD122 (anti-CD40) | | Ongoing | Phase I ongoing | |
| Anti-CD22-calicheamicin (CMC-544) | Humanized IgG4 | Thrombocytopenia | 69, relapsed FL | Fayad et al |

TABLE 2-continued

Selected anti-B cell antibodies in clinical trials with non-Hodgkin lymphoma patients

| Antibody name | Type | DLT | Objective response rate, (%, NHL entity)/clinical data | Reference |
|---|---|---|---|---|
| BL22 (anti-CD22 coupled to *pseudomonas* exotoxin) | | Hemolytic uraemic syndrome | Responses in hairy cell leukemia | |

The extra domain B (EDB) of fibronectin is one of the best-characterized markers of angiogenesis described so far (Zardi et al., Embo J. 1987; 6:2337-2342; Kaspar et al., Int J Cancer. 2006; 118:1331-1339). This 91-amino acid type III homology domain can be inserted into the fibronectin molecule during active tissue remodeling by a mechanism of alternative splicing (Zardi et al., supra). EDB is essentially undetectable in healthy adult tissues but is highly abundant in the vasculature of many aggressive solid tumors. The tumor-targeting ability of the high-affinity human antibody L19 (Pini et al., J Biol. Chem. 1998; 273:21769-21776), specific to EDB, has been well established both in animal models of cancer (Tarli et al., Blood. 1999; 94:192-198; Borsi et al., Int J. Cancer. 2002; 102:75-85; Berndorff et al., J Nucl Med. 2006; 47:1707-1716; Berndorff et al., Clin Cancer Res. 2005; 11:7053s-7063s; Demartis et al., Eur J Nucl Med. 2001; 28:534-53) and in patients with solid tumors (Santimaria et al., Clin Cancer Res. 2003; 9:571-579). Recently, ED-B expression was also found in the majority of lymphoma-infiltrated tissue samples from various Non-Hodghkin lymphoma patients (Sauer et al., 2006).

Based on current knowledge about antibody-based cancer therapies in particular when combined with rIL-2 or similar cytokines, it was surprising to find in combination therapy experiments in mice, that the combination of rituximab with the L19-IL2 fusion induced complete eradications of established Ramos lymphomas in 4 of 5 mice in the high dose L19-IL2 group (L19-IL2$_{high\ dose}$ vs. saline: P<0.00001), with 3 of 4 CRs (complete remessions) already being achieved after 3 injections. In fact, the immunocytokine was remarkably more potent than the corresponding equimolar amount of unconjugated rIL-2 in combination with rituximab (L19-IL2$_{high\ dose}$ vs. rIL-2$_{high\ dose}$: P<0.001). Notably, even L19-IL2 at the lowest dose level combined with rituximab still displayed an excellent therapeutic activity (L19-IL2$_{low\ dose}$ vs. saline: P<0.00001; L19-IL2$_{low\ dose}$ vs. rIL-2$_{low\ dose}$: P<0.00001), inducing CRs in 4 of 5 cases after 4 cycles of therapy, whereas even a three-fold higher dose of the non-targeted cytokine combined with rituximab was only able to retard tumor growth (L19-IL2$_{low\ dose}$ vs. rIL-2$_{high\ dose}$: P<0.001).

Therefore, in one embodiment, the invention relates to a combination comprising at least
(i) a fusion protein comprising an antibody-part specifically recognising ED$_b$-fibronectin and an Interleukin-2 part and
(ii) a molecule binding to B cells, B cell progenitors and/or their cancerous counterpart.

In a preferred embodiment, the molecule binding to B cells, B cell progenitors and/or their cancerous counterpart is specifically binding to CD20, CD23, CD22, CD40, CD80, HLA-DR or Hu1D10.

In a preferred embodiment the molecule binding to B cells, B cell progenitors and/or their cancerous counterpart is selected from an antibody, antibody fragment or antibody mimetic.

Preferred is a molecule specifically binding to CD20, CD23, CD22, CD40 or CD80 which is a full-length antibody or antibody fragment, or a fusion protein thereof.

In a particularly preferred embodiment, the antibody or antibody fragment, or fusion protein thereof is specifically binding to CD20.

In one embodiment, the invention relates to a combination comprising at least
(i) a fusion protein comprising an antibody-part specifically recognising ED$_b$-fibronectin and an Interleukin-2 part and
(ii) a molecule specifically binding to CD20.

In a further embodiment, the invention relates to a combination comprising at least
(i) a fusion protein comprising an antibody-part specifically recognising ED$_b$-fibronectin and an Interleukin-2 part and
(ii) a molecule specifically binding to cells expressing CD20.

In a particularly preferred embodiment, the molecule specifically binding to cells expressing CD20 and/or specifically binding to CD20 is an antibody or antibody fragment specifically binding to CD20.

In a preferred embodiment, the antibody-part of (i) specifically binds to the EDb-domain of fibronectin (FN). Such antibodies are known in the prior art and are e.g. described in WO 97/45544.

In another embodiment, the antibody specifically recognizing EDb-fibronectin binds to a cryptic epitope. An example for such antibody is the BC-1 antibody.

Preferably, such antibody which binds to the EDb-domain of fibronectin exhibits a high affinity for the EDb-domain of FN, in particular, the antibody binds to the EDb fibronectin domain with nanomolar or subnanomolar affinity. Such antibodies are known in the prior art and are e.g. described in WO99/58570.

In particular preferred is the L19 antibody.

The antibody part specifically recognizing EDb fibronectin, in particular the L19 antibody, can be employed in various antibody formats. Preferred antibody formats are full IgG, Fab, (Fab')$_2$, scFv, diabody, minibody or small immunoprotein (SIP) format. Especially preferred are the full IgG, scFv and SIP format for the L19 antibody. Most preferred is the L19 antibody in the scFv format. Several immunoprotein formats are known in the prior art, e.g. based on the CH3 domain or the $\epsilon_{s2}$-CH4 domain of IgE. The preferred SIP format for L19 based on the $\epsilon_{s2}$-CH4 domain of IgE and L19 in full IgG format are for example described in WO03/076469.

In a further preferred embodiment, the antibody-part contains at least one CDR sequence of the L19 antibody.

In an especially preferred embodiment, the antibody-part comprises the CDR sequences of the L19 antibody, in particular it comprises the sequences according to SEQ ID no. 6 to 11.

In a further preferred embodiment, the antibody-part comprises the VL and VH chain of the L19 antibody. In a preferred embodiment, it comprises least one VH chain according to SEQ ID No. 1 or at least one VL chain according to SEQ ID No. 2. In an especially preferred embodiment, it comprises least one VH chain according to SEQ ID No. 1 and at least one VL chain according to SEQ ID No. 2.

In a further preferred embodiment, the antibody-part comprises one VH chain according to SEQ ID No. 1 and one VL chain according to SEQ ID No. 2. In a further preferred embodiment, the antibody-part comprises two VH chains according to SEQ ID No. 1 and two VL chains according to SEQ ID No. 2.

In a further preferred embodiment, the VH and the VL chains are connected by an antibody linker.

In a preferred embodiment, the antibody linker comprises a sequence according to SEQ ID No. 3, or a sequence having at least 90% identity to the sequence according to SEQ. ID. No. 3.

The antibody-part specifically binding to EDb-fibronectin is fused to Interleukin-2. Both parts may be fused directly, or may be fused via a linker, in particular by a peptidic fusion protein linker. Preferably, the fusion protein linker has a length of 1 to 30 amino acids. In a particularly preferred embodiment, the fusion protein linker comprises a sequence according to SEQ ID No. 5.

In another particularly preferred embodiment, the Interleukin-2 is human Interleukin-2 (human IL-2).

Interleukin-2 may be produced recombinantly or may be isolated from human tissue, preferably it is produced recombinantly (rIL-2). In an especially preferred embodiment, the Interleukin-2 part comprises a sequence according to SEQ. ID. No. 4, or a functional variant thereof.

The fusion protein may be monomeric, or multimeric, e.g. dimeric. Dimeric or other multimeric forms may be formed covalently or non-covalently. E.g. L19(scFv)-IL2 may form non-covalent homodimers.

The fusion proteins are preferably produced recombinantly using methods known to the skilled person. In particular, prokaryotic or eukaryotic expression systems, e.g. yeast or mammalian expression systems, can be used.

The combination of the present invention further comprises a molecule binding to B cells, B cell progenitors and/or their cancerous counterpart.

In one embodiment of the present invention, the molecule binding to B cells, B cell progenitors and/or their cancerous counterpart is labelled, in particular radioactively labelled. Preferably, the labelling is a covalent labelling.

In an especially preferred embodiment, the labelled molecule binding to B cells, B cell progenitors and/or their cancerous counterpart, is a radioactively labelled anti-CD20 antibody. Various radioactive labels are used in medicine.

Particularly useful radioactive isotopes for labelling antibodies and proteins are $^{90}$Y, $^{111}$In and $^{131}$I-labelled. In an especially preferred embodiment, the anti-CD20 antibody is labelled with $^{90}$Y, $^{111}$In or $^{131}$I.

In a particularly preferred embodiment, the radioactively labeled anti-CD20 antibody is selected from Y-90-Ibritumomab-Tiuxetan (Y90-ZEVALIN® or -ZEVALIN®) and I-131 tositumomab (BEXXAR®). Y-90-Ibritumomab-Tiuxetan and its production is for example disclosed in EP 0 669 836 as Y2B8 (Yttrium-[90]-labeled 2B8-MX-DTPA).

In a preferred embodiment, the combination of the present invention further comprises a molecule specifically binding to CD20. In an especially preferred embodiment, this molecule is an antibody or antibody fragment, or a fusion protein thereof.

Particularly preferred are anti-CD20 antibodies which exhibit ADCC activity.

In a further preferred embodiment, the anti-CD20 antibody is selected from rituximab, Ocrelizumab, PRO131921, Veltuzumab, Ofatumumab, AME-133, and GA-101.

In a preferred embodiment of the invention, the antibodies specifically binding to CD20 are in full IgG, Fab, (Fab)$_2$, scFv, diabody, minibody or small immunoprotein (SIP) format.

Also, the anti-CD20 antibody may be monomeric or multimeric, e.g. dimeric. Multimeric antibodies may be homomeric or heteromeric. E.g. a bivalent antibody may be used, wherein one part specifically binds to CD20 and another part binds to another target. Also, the molecule specifically binding to CD20 may comprise further effectors, in particular it may be labelled radioactively. In this embodiment of the present invention, ZEVALIN® or BEXXAR® may be used, as described above.

A particularly preferred anti-CD20 antibody is rituximab, in particular RITUXAN® (also called MABTHERA® or IDEC-C2B8). RITUXAN® is a genetically engineered chimeric murine/human monoclonal antibody directed against the CD20 antigen found on the surface of normal and malignant B lymphocytes. The antibody is an IgG1 kappa immunoglobulin containing murine light- and heavy-chain variable region sequences and human constant region sequences. rituximab is disclosed e.g. in U.S. Pat. No. 5,843,439; 5,776,456 and 5,736,137.

In a more preferred embodiment, the combination comprises rituximab and L19-IL2.

In an even more preferred embodiment the L19 antibody is in scFv format.

Particularly preferred is L19-IL2 as described in Carnemolla et al., Blood. 2002; 99:1659-1665.

Another embodiment of the present invention relates to a combination as described above, for use as a medicament.

A further embodiment of the present invention relates to a combination as described above, for use as a medicament for treating cancer.

In a preferred embodiment, the cancer is a lymphoma, preferably a B-cell lymphoma. Most preferred is the use of the combination of the present invention for treating B-cell Non-Hodgkin lymphoma (B-NHL).

In a further preferred embodiment, the B-cell lymphoma is refractory or relapsed B-cell lymphoma or a lymphoma resistant to rituximab-monotherapy.

The invention further relates to a method of treating cancer, wherein a combination of the present invention is administered to a cancer patient in therapeutically effective amount. Preferably, the cancer is a lymphoma, preferably a B-cell lymphoma, in particular a NHL.

A further embodiment of the present invention relates to a combination as described above, for use as a medicament for treating autoimmune diseases, in particular chronic autoimmune diseases.

In a preferred embodiment, the autoimmune disease is rheumatoid arthritis, Crohn's disease, colitis ulcerosa or autoimmune hemolytic anemia.

The patient can be any mammal, preferably the patient is a human.

Various administration routes are possible, e.g. intravenous, subcutaneous or intraperitoneal administration, wherein the intravenous administration is preferred.

Also, the fusion protein specifically recognizing EDb fibronectin and the molecule binding to B cells, B cell progenitors and/or their cancerous counterpart may be administered at the same time or at different time points. Moreover, the combination may be administered once or several times to a patient. Also, it is possible, that one component of the combination is administered once, and the other component is administered several times.

Typically, if rituximab and L19-IL2 are administered as combination therapy, they may be administered to a patient at the same time point, as this allows easier administration schedules. For examples, rituximab and L19-IL2 both may be administered i.v. once or twice per day in time intervals ranging from few days up to 3 months. Also, one or more treatment rounds are possible.

Moreover, the amount administered may vary. For example, rituximab may be administered in an amount of about 20 to 500 mg/m$^2$, preferably in an amount of about 100 to 400 mg/m$^2$, in particular of about 375 mg/m$^2$ rituximab per administration. Typically, rituximab is administered on Day 1 of a 2-, 3-, or 4-week treatment schedule with up to 6-8 treatment cycles (remission induction), although other administration schedules are possible.

Therapeutic formulations of the active agents used in accordance with the present invention are prepared for storage by mixing an active agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Exemplary anti-CD20 antibody formulations are described in WO 98/56418. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5. Lyophilized formulations adapted for subcutaneous administration are described in WO 97/04801. Such lyophilized formulations may be reconstituted with a suitable diluent to a high protein concentration and the reconstituted formulation may be administered subcutaneously to the patient to be treated herein.

Also, for the fusion protein the amount to be administered may vary. Typically, the amount of L19-IL2 to be administered per administration is about 1 to 10×10$^6$ IU/m$^2$, in particular about 5 to 50×10$^6$ IU/m$^2$, especially about 10 to 30×10$^6$ IU/m$^2$.

It is also possible that the administered amount varies over time; e.g. the amount of rituximab and/or L19-IL2 may be increased or decreased for one or more administration rounds.

Also, a maintenance treatment, in particular with rituximab or L19-IL2 alone, may follow the combination treatment phase.

Also, it is possible to support with L19-IL2 the treatment with antibody-containing combination therapies against B-NHL, in particular, chemoimmunotherapeutic regimens (e.g. R-CHOP).

Antibody linker is any linker, preferably a peptide linker, which is suitable for linking Vh and Vl domains. Suitable linkers are for example described in Bird et al, Science, 242, 423-426, 1988; Huston et al, PNAS USA, 85, 5879-5883, 1988, EP 0 573 551; EP 0 623679 and EP 0 318554, which documents are introduced by reference.

Fusion protein linkers are linkers suitable for linking an antibody or antibody-fragment and a second biologically active protein, preferably the linker is peptidic. Suitable linkers are described in EP 0 573 551; EP 0 623679 and EP 0 318554, which documents are introduced by reference. In particular, suitable linkers are described in EP 0 623679.

"Specifically binding" or "specifically recognizing" as used herein refers to binding to the corresponding target. Typically, the binding molecule, antibody, antibody fragment or antibody mimetic binds with an affinity of at least about 1×10$^{-7}$ M, preferably of at least about 1×10$^{-9}$ M, and binds to the predetermined target with an affinity that is at least two-fold greater than its affinity for binding to a non-specific target (e.g. BSA, casein) other than the predetermined target or a closely-related target.

"Antibody" as used herein encompasses full length antibodies, comprising native antibodies, monoclonal antibodies, polyclonal antibodies and multispecific antibodies (e.g., bispecific antibodies), human antibodies, humanized antibodies, chimeric antibodies, and full IgG antibodies, as well as antibody fragments.

The term "antibody fragment" refers to a portion of a full length antibody, in which a variable region or a functional capability is retained, namely the specific binding to the target. Examples of antibody fragments include, but are not limited to, a Fab, Fab', F(ab')2, Fd, Fv, scFv and scFv-Fc fragment, a diabody, a linear antibody, small immunoprotein formats, a single-chain antibody, a minibody, a diabody formed from antibody fragments, and multispecific antibodies formed from antibody fragments. Antibody fragments are usually smaller than full antibodies. Thereby, the pharmacokinetics are different and some antibody fragments only consist of one polypeptide chain, which can make production easier. However, such fusion proteins comprising antibody fragments often suffer from a reduced stability. Preferably, the antibody fragment is in scFv, (scFv)2, or small immunoprotein format. The small immunoprotein format can be a format based on a CH3-domain (for example described in U.S. Pat. No. 5,837,821) or $\epsilon S_2 CH4$-domain of human IgE (for example described in WO 03/076469).

The term "monoclonal antibody" (mAb) refers to an antibody obtained from a population of substantially homogeneous antibodies; that is, the individual antibodies comprising the population that are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Koehler et al., 1975, Nature 256:495, or recombinant DNA methods known in the art (see, e.g., U.S. Pat. No. 4,816,567). In another example, monoclonal antibodies can also be isolated from phage antibody libraries, using techniques described in Clackson et al., 1991, Nature 352: 624-628, and Marks et al., 1991, J. Mol. Biol. 222: 581-597.

In contrast, the antibodies in a preparation of polyclonal antibodies are typically a heterogeneous population of immunoglobulin isotypes and/or classes and also exhibit a variety of epitope specificity.

The term "chimeric" antibody as used herein is a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence.

Certain types of antibody fragments can be generated by enzymatic treatment of a full-length antibody. Papain digestion of antibodies produces two identical antigen-binding fragments called "Fab" fragments, each with a single antigen-binding site, and a residual "Fc" fragment, so called because of its ability to crystallize readily. The Fab fragment also contains the constant domain of the light chain and the CH1 domain of the heavy chain. Pepsin treatment yields a F(ab')2 fragment that has two antigen-binding sites and is still capable of cross-linking antigen.

Fab' fragments differ from Fab fragments by the presence of a few additional residues at the C-terminus of the CH1 domain, including one or more cysteines from the antibody hinge region. Fab-SH is the designation herein for a Fab' in which the cysteine residue(s) of the constant domains bear a free thiol group. F(ab')2 antibody fragments are pairs of Fab' fragments linked by cysteine residues in the hinge region. Other chemical couplings of antibody fragments are also known.

"Fv" is a minimum antibody fragment that contains a complete antigen-recognition and binding site consisting of a dimer of one heavy and one light chain variable domain in tight, non-covalent association. In this configuration, the three CDRs of each variable domain interact to define an antigen-binding site on the surface of the VH VL dimer. Collectively, the six CDRs confer antigen-binding specificity to the antibody.

A "single-chain Fv" or "scFv" antibody fragment is a single chain Fv variant comprising the VH and VL domains of an antibody, in which the domains are present in a single polypeptide chain and which is capable of recognizing and binding antigen. The scFv polypeptide optionally contains a polypeptide linker positioned between the VH and VL domains that enables the scFv to form a desired three-dimensional structure for antigen binding (see, e.g., Pluckthun, 1994, In The Pharmacology of Monoclonal Antibodies, Vol. 113, Rosenburg and Moore eds., Springer-Verlag, New York, pp. 269-315).

The term "diabodies" refers to small antibody fragments having two antigen-binding sites. Each fragment contains a heavy chain variable domain (VH) concatenated to a light chain variable domain (VL). By using a linker that is too short to allow pairing between the two domains on the same chain, the linked VH-VL domains are forced to pair with complementary domains of another chain, creating two antigen-binding sites.

Diabodies are described more fully, for example, in EP 404,097; WO 93/11161; and Hollinger et al., 1993, Proc. Nat. Acad. Sc. USA 90: 6444-6448.

A humanized antibody or a humanized antibody fragment includes an immunoglobulin amino acid sequence variant, or fragment thereof, which is capable of binding to a predetermined antigen and which, comprises one or more framework regions (FRs) having substantially the amino acid sequence of a human immunoglobulin and one or more CDRs having substantially the amino acid sequence of a non-human immunoglobulin. This non-human amino acid sequence is referred to herein as an "import" sequence, which is typically taken from an "import" antibody domain, particularly a variable domain. In general, a humanized antibody includes at least the CDRs or HVLs of a non-human antibody, inserted between the FRs of a human heavy or light chain variable domain.

"Native antibodies" are defined herein as heterotetrameric glycoproteins, typically of about 150,000 daltons, composed of two identical light (L) chains and two identical heavy (H) chains. Each light chain is covalently linked to a heavy chain by one disulfide bond to form a heterodimer. The heterotetramer is formed by covalent disulfide linkage between the two identical heavy chains of such heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain (VH), followed by three or four constant domains (CH1, CH2, CH3, and CH4), as well as a hinge region between CH1 and CH2. Each light chain has two domains, an amino-terminal variable domain (VL) and a carboxy-terminal constant domain (CL). The VL domain associates non-covalently with the VH domain, whereas the CL domain is commonly covalently linked to the CH1 domain via a disulfide bond. Particular amino acid residues are believed to form an interface between the light and heavy chain variable domains (Chothia et al., 1985, J. Mol. Biol. 186:651-663.) The term "hypervariable" refers to the fact that certain sequences within the variable domains differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917.

Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain.

The term "label" refers to a detectable compound or composition that is conjugated directly or indirectly to the antibody. The label may itself be detectable (e.g., radioisotope labels or fluorescent labels) or, in the case of an enzymatic label, may catalyze chemical alteration of a substrate compound or composition that is detectable.

Although fibronectins (FNs) are the product of the single FN gene, the resulting protein can exist in multiple forms which—apart from posttranslational modifications—arise from alternative splicing of its primary RNA transcript. This polymorphism which leads to as many as 20 different isoforms in human FN, thereby generating FNs with different solubility, cell adhesive and ligand-binding properties, provides cells with the possibility to modify the composition of the extracellular matrix (ECM) in a tissue-specific manner. Alternative splicing takes place in three regions of the primary RNA transcript: Exon usage or skipping leads to either inclusion or omission of two type-III repeats, extra-domain B (EDB or ED-B, also termed EIIIB or EDIII), which is inserted between FN type-III repeats III7 and III8, or/and extra-domain A (EDA, also termed EIIIA or EDI), inserted between FN type-III repeats III11 and III12. This type of splicing occurs in many vertebrates, including *Xenopus*, chicken, rat, dog and human.

"ED-B domain" is to be understood as the extra-domain B of human fibronectin. It is often referred to as EDb, EIIIB or EDII.

"Antibody mimetics" are understood as binding molecules based on protein frameworks ("scaffolds") which specifically bind to the target and which are distinct from antibodies and antibody fragments. Such scaffolds are described in Binz et al., 2005, Nat. Biotechnol. 23, 1257-1268. Antibody mimetics specifically binding to ED-B fibronectin are described in Grabulovski et al., J. Biol. Chem., 2007, 282:3196-3204.

"Interleukin-2" according to the present invention refers to mammalian Interleukin-2, preferably human Interleukin-2 and functional variants thereof. Functional variants of Interleukin-2 are variants of human Interleukin-2 which exhibit at least 10%, but more preferably more than 50%, and even more preferred more than 90% of the activity of native human Interleukin-2. Interleukin-2 activities are activities of Interleukin-2 in biochemical assays or in vivo, in particular Interleukin-2 activity can be measured by the effect on proliferation and/or differentiation of activated T and B lymphocytes and of natural killer cells and/or induction of cytotoxic T cell activity and/or NK/lymphokine activated killer (LAK) antitumour activity (Meazza R, Marciano S, Sforzini S, et al. Analysis of IL-2 receptor expression and of the biological effects of IL-2 gene transfection in small-cell lung cancer. Br. J. Cancer. 1996; 74: 788-795). In particular, functional variants are cystein-125 muteins of Interleukin-2 as described in EP 0109748 and other muteins, including cystein muteins as described in EP136489, in particular serine 125-Interleukin-2. Also, the N-terminus of hIL.2 variants may be altered without significantly affecting the activity, in particular the N-terminal 1-5 amino acids, especially preferred the N-terminal Alanine may be deleted or altered, preferably deleted. Moreover, the Interleukin-2 may contain altered or deleted post-translational modifications, in particular the glycosylation pattern may be altered or missing. Different or absent glycosylation may be obtained e.g. either by mutating the sequence or by expression of the fusion protein in an appropriate host. For example, Aldesleukin, which is approved for metastatic RCC, is unglycosylated des-alanyl-1, serine-125 human interleukine-2 produced in *E. coli*.

FIGURE LEGEND

FIG. 1. Immunohistochemistry with L19 antibody reveals EDB expression in B-cell lymphoma xenografts. Immunohistochemical staining using the antibody L19, specific to EDB fibronectin, revealed a strong expression of this fibronectin isoform with a prominent vascular pattern of staining in Ramos lymphoma xenografts (left panel). The staining is similar to the staining pattern of L19 in solid tumors, as exemplified with the U87 glioblastoma xenograft (right panel). For negative control, the primary antibody was omitted. Scale bars, 100 μm.

Figure 2:
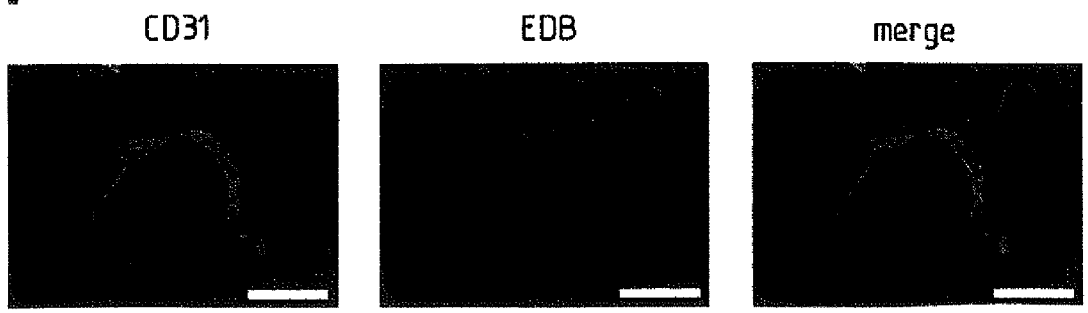

FIG. 2. In vivo localization experiments: ex vivo immunofluorescence (A) and quantitative biodistribution studies (B). The in vivo targeting performance of the L19 antibody was tested in the subcutaneous SCID/Ramos lymphoma model. (A) Lymphoma-bearing mice were injected with L19-SIP, chemically labeled with the fluorophore Cy3. The figure shows a 2-color fluorescence microscopic image of a lymphoma section 24 h after injection, confirming the antibody localization (red) on tumor vascular structures. An anti-CD31 antibody has been applied ex vivo to outline endothelial cells and was detected with an Alexa Fluor 488 anti-rat IgG antibody (green). Scale bars, 100 μm. (B) Quantitative biodistribution results were obtained 24 h and 48 h after injection of $^{125}$I-radiolabeled L19-SIP into lymphoma-bearing animals (n≥3 for each time point). Mean targeting results are expressed as percent injected dose per gram of tissue (% ID/g±SD). Forty-eight hours after injection, a selective accumulation and retention of the antibody in the lymphoma tissue could be observed, with tumor-to-blood ratios of 4.8 and tumor-to-organs ratios ranging from 3.8 to 17.3.

Figure 3:
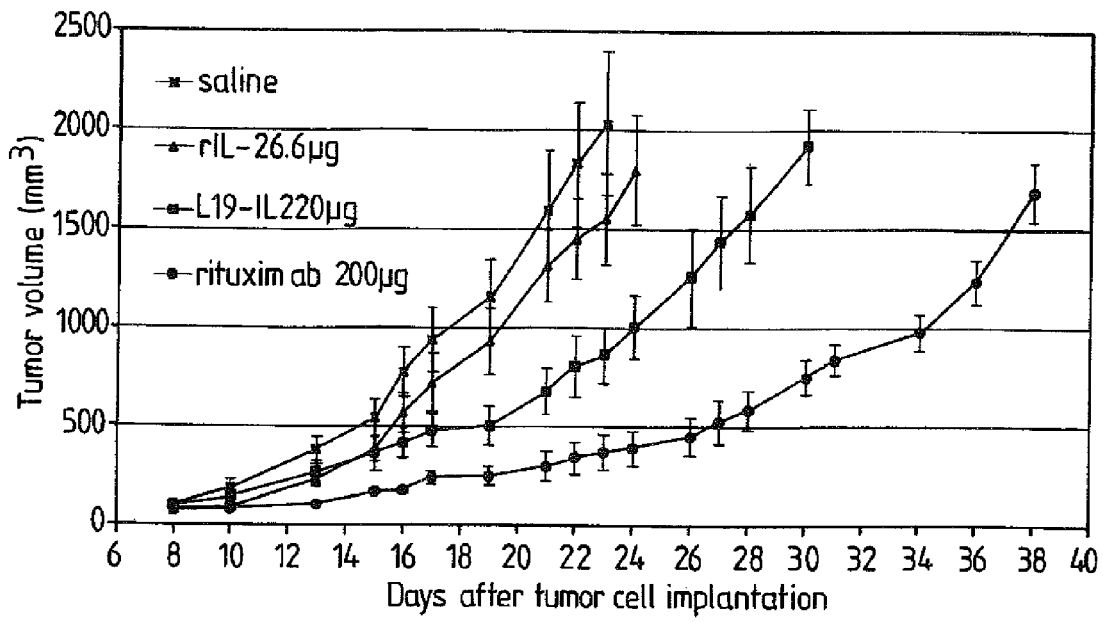

FIG. 3. Effect of single-agent L19-IL2, unconjugated IL-2 and rituximab on lymphoma growth. SCID mice bearing established s.c. Ramos lymphoma xenografts were injected i.v. with either the vascular targeting L19-IL2 fusion protein (■; 20 μg), the corresponding dose of untargeted rIL-2 (▲; 6.6 μg), rituximab (●; 200 μg), or control saline (X) on days 8, 11, 14, and 17 after tumor cell implantation. Single-agent L19-IL2 and single-agent rituximab both delayed tumor growth significantly (P=0.024 and P=0.004, respectively). In contrast, unconjugated rIL-2 did not exhibit significant therapeutic activity (P=0.383), indicating the contribution of the targeted delivery of IL-2 to the therapeutic effect (L19-IL2 vs. IL-2: P=0.044).

Figure 4:
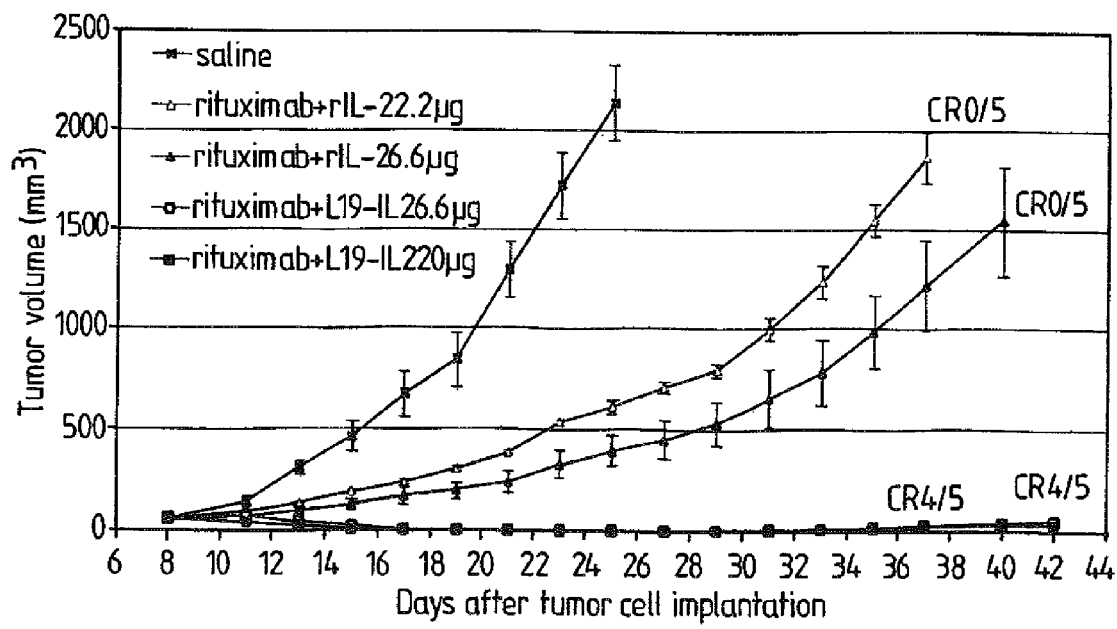

FIG. 4. Therapeutic effect of L19-IL2 and unconjugated IL-2 in combination with rituximab. SCID mice bearing established s.c. lymphoma xenografts were injected i.v. with either saline (X), 200 μg rituximab+low dose unconjugated IL-2 (Δ; 2.2 μg), 200 μg rituximab+high dose unconjugated IL-2 (▲; 6.6 μg), 200 μg rituximab+low dose L19-IL2 (□; 6.6 μg, corresponding to 2.2 μg IL-2), or 200 μg rituximab+high dose L19-IL2 (■; 20 μg, corresponding to 6.6 μg IL-2) on days 8, 11, 14, and 17. L19-IL2 in combination with rituximab was highly efficacious, inducing complete remissions in 4 of 5 mice in the low dose as well as in the high dose L19-IL2 group. In contrast, unconjugated rIL-2 in combination with rituximab did not induce tumor regressions and all tumors continued to grow. All mice with CRs remained tumor-free for a period of at least 42 days.

Figure 5:
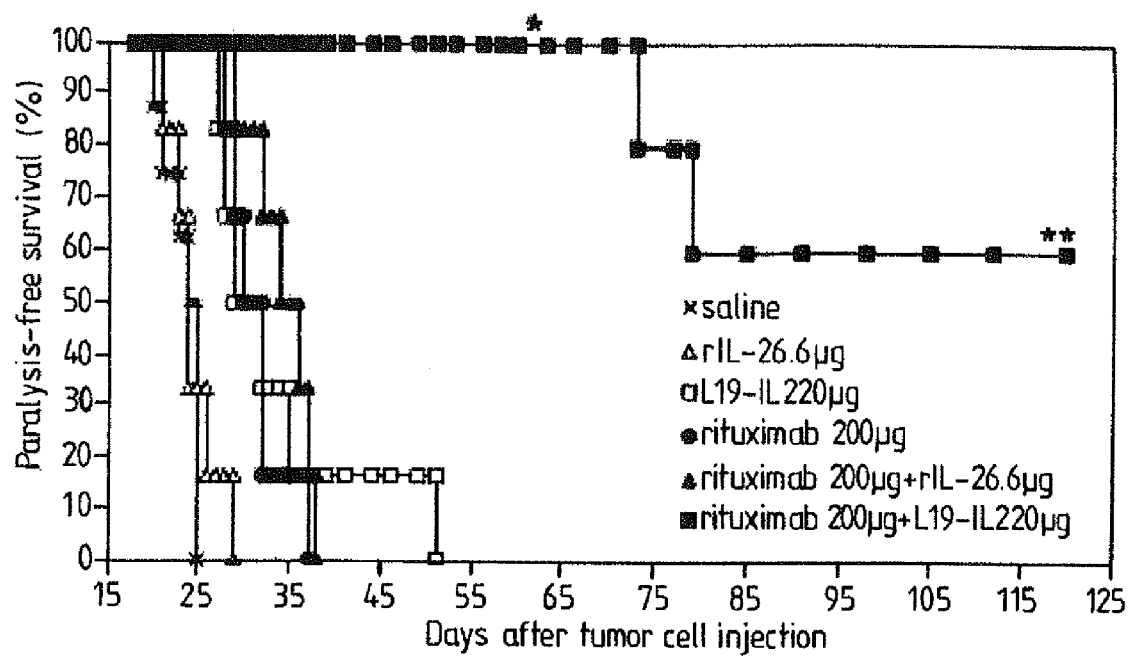

FIG. 5. Therapeutic effect of L19-IL2, IL-2 and rituximab in mono- and combination therapies in the disseminated lymphoma model. SCID mice (n≥6) were injected i.v. with 2×10$^6$ Ramos lymphoma cells and treated 8 days later according to the following regimens: untargeted IL-2 (6.6 μg), L19-IL2 (20 μg), rituximab (200 μg), rituximab (200 μg)+IL-2 (6.6 μg), rituximab (200 μg)+L19-IL2 (20 μg), or control saline (In detail, to model systemic disease, SCID mice were injected i.v. with 2×10$^6$ Ramos lymphoma cells resuspended in 200 μL PBS. Dissemination and growth of B-cell lymphoma was allowed to occur for 8 days before the initiation of therapy. Mice were randomly divided into 6 groups (≥6 mice per group) and injected i.v. with either saline, 20 μg L19-IL2, 6.6 μg unconjugated rIL-2, or 200 μg rituximab (single-agent treatment groups), or 200 μg rituximab in combination with 20 μL19-IL2, or 200 μg rituximab in combination with 6.6 μg unconjugated rIL-2 (combination treatment groups), on days 8, 11, 14, and 17 (Q3Dx4). Mice were monitored daily for the presence of hind-leg paralysis or signs of a deteriorating condition whereupon mice were sacrificed and scored as dead. Survival was recorded for analysis of therapeutic efficacy).

Figure 6:
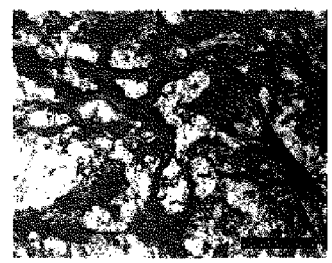
Figure 6:
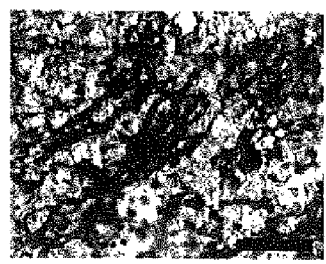
Figure 6:
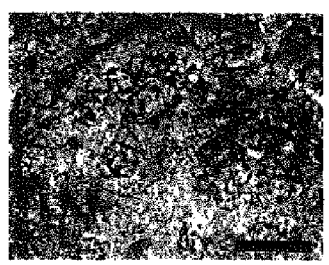

FIG. 6. Target validation in human lymphoma samples. EDB was found to be expressed in neovascular structures of human B-cell lymphoma entities, including the frequent subtypes diffuse large B-cell lymphoma and Burkitt lymphoma. Scale bars, 100 μm.

Figure 7:
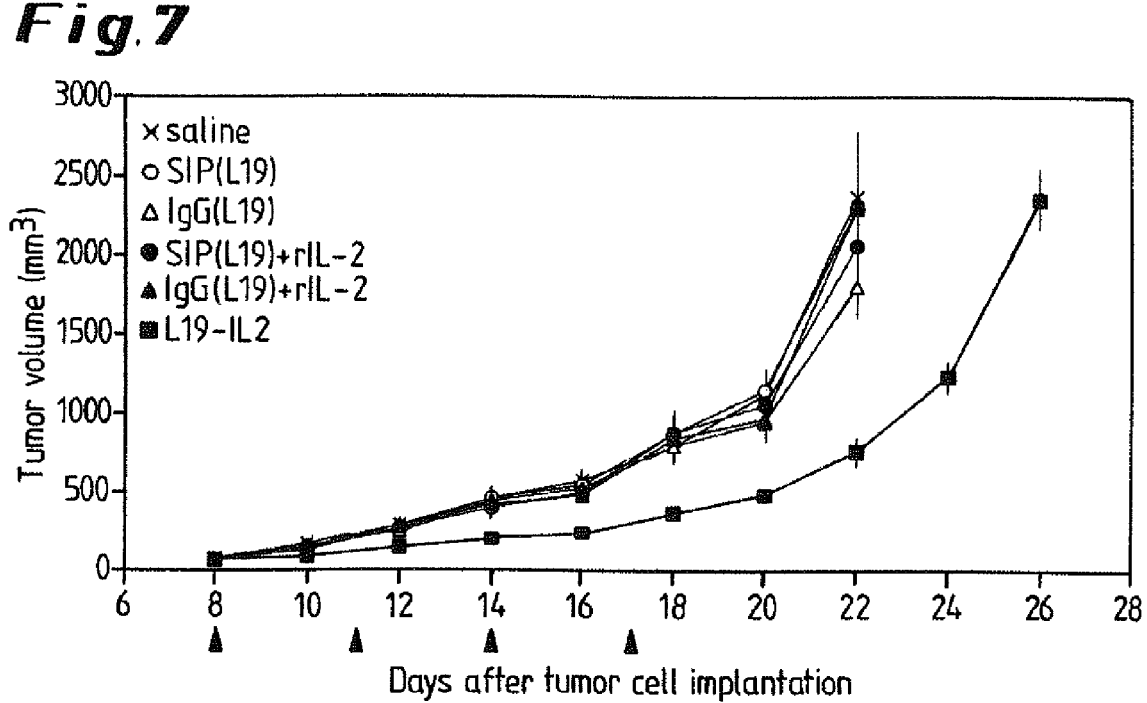

FIG. 7. While the fusion protein L19-IL2 reproducibly inhibited lymphoma growth (P=0.031), equimolar amounts of naked L19 in SIP or IgG format were therapeutically inactive when administered alone or in combination with free rIL-2.

EXAMPLES

Materials and Method

Animals and Cell Lines

Six- to 8-week-old female CB17/lcr SCID mice were obtained from Charles River Laboratories (Sulzfeld, Germany). All mice were housed in microisolator units and provided with sterile food and water ad libitum throughout the studies. The EBV-negative human B cell lymphoma cell line Ramos[44] was purchased from the American Type Culture Collection (ATCC, Manassas, Va.). Cells were maintained in log-phase growth in RPMI 1640 medium adjusted to contain 2 mM L-glutamine, 10 mM HEPES, 1 mM sodium pyruvate, 4.5 g/L glucose, 1.5 g/L bicarbonate, 10% heat-inactivated fetal bovine serum, 100 U/mL penicillin, and 100 µg/mL streptomycin. The human follicular lymphoma cell line DoHH-2 was obtained from the German Resource Centre for Biological Material (DSMZ, Braunschweig, Germany).

Antibodies and Reagents

L19 is a vascular targeting antibody directed against the EDB domain of fibronectin. The expression, purification and characterization of L19 in SIP format (small immunoprotein) and the L19-IL2 fusion protein have been described previously in Borsi et al. (Int J. Cancer. 2002;102:75-85) and Carnemolla et al. (Blood. 2002;99:1659-1665). Recombinant human IL-2 (Proleukin, 18×10⁶ IU) was obtained from Prorero Pharma (Liestal, Switzerland) and the chimeric human IgG1 anti-CD20 monoclonal antibody rituximab (MABTHERA®) from Roche (Reinach, Switzerland).

Immunohistochemistry

For immunohistochemistry on Ramos xenograft tumors, 10 µm cryostat sections of frozen samples were fixed in ice-cold acetone, rehydrated in TBS (50 mmol/L Tris, 100 mmol/L NaCl pH 7.4), and blocked with 20% FCS (Invitrogen, Basel, Switzerland). L19-SIP was added onto the sections in a final concentration of 10 µg/mL. Bound primary antibody was detected with rabbit anti-human IgE antibody (Dako, Glostrup, Denmark) followed by biotinylated goat anti-rabbit IgG antibody (Biospa, Milan, Italy) and streptavidin-alkaline phosphatase complex (Biospa). Fast Red TRSalt (Sigma) was used as the phosphatase substrate. Immunohistochemical analysis of EDB expression in human lymphoma samples was performed using biotinylated L19-SIP and streptavidin-alkaline phosphatase (SAP). Sections were counterstained with hematoxylin, mounted with Glycergel mounting medium (Dako) and analyzed with an Axiovert S100 TV microscope (Zeiss, Feldbach, Switzerland).

Immunohistochemistry on human lymphoma samples was performed as on lymphoma xenografts, however, biotinylated L19-SIP was used as primary antibody and detected with steptavidin-alkaline phosphatase complex (Biospa).

Ex Vivo Fluorescence Experiments

L19-SIP was labeled with Cy3-NHS ester, a fluorescent cyanine compound, following the manufacturer's recommendation (Amersham Pharmacia, Dübendorf, Switzerland). 120 µg of L19-Cy3 conjugate were injected intravenously (i.v.) into the lateral tail vein of lymphoma-bearing mice. Mice were sacrificed 24 h after injection, and tumors were excised, embedded in cryoembedding compound (Microm, Walldorf, Germany) and stored at −80° C. 10 µm sections were cut, dried at 37° C. for 15 min and fixed with 4% paraformaldehyde for 15 min at room temperature. Rat anti-CD31 antibody (BD Pharmingen) was applied to outline endothelial cells using Alexa Fluor 488 rabbit anti-rat IgG as secondary antibody (Invitrogen). Images were captured on an Axioskop 2 Mot plus microscope equipped with an AxioCam MRc camera (Zeiss).

Quantitative Biodistribution

To evaluate the in vivo targeting performance quantitatively, biodistribution analyses using radiolabeled antibody preparations were performed as described before (Camemolla et al., 2002). Briefly, purified SIP(L19) was radioiodinated with 125I and injected i.v. into SCID mice bearing s.c. implanted Ramos lymphoma xenografts or into Balb/c mice bearing systemic syngeneic A20 lymphomas (10 µg, 12.2 µCi per mouse). Mice were sacrificed either 24 h or 48 h after injection, at least three animals were used for each time point. Organs were weighed and radioactivity was counted using a Cobra γ counter (Packard, Meriden, Conn.). Radioactivity content of representative organs was expressed as the percentage of the injected dose per gram of tissue (% ID/g±SE).

Localized Lymphoma Xenograft Model

1×10⁷ Ramos lymphoma cells or DoHH-2 (1×10⁷) lymphoma were injected s.c. into the flank of 6- to 8-week-old female CB17/lcr SCID mice on day 0. When tumors were established and clearly palpable (50-100 mm³, day 8 after injection), mice were staged to maximize uniformity among the groups and injected into the lateral tail vein with either 20 µL19-IL2 (corresponding to 6.6 µg or 118000 IU rIL-2), 6.6 µg untargeted rIL-2, 200 µg rituximab, or control saline in a volume of 100 µL on days 8, 11, 14 and 17 (Q3Dx4). For combination therapy studies, L19-IL2 (6.6 and 20 µg, corresponding to 2.2 and 6.6 µg of "free" rIL-2, respectively), or unconjugated rIL-2 (2.2 and 6.6 µg) were administered in combination with rituximab (200 µg) by separate i.v. injections on days 8, 11, 14, and 17. To test whether the L19 antibody alone was therapeutically active, mice were treated with equimolar amounts of L19 in SIP (x.x µg) or IgG (x.x µg) format, alone or in combination with free rIL-2 (6.6 µg). Treatment schedule for all agents (in mono- and combination therapies) was every third day for four (Ramos) or three (DoHH-2) injections in total (Q3Dx4 or Q3Dx3, respectively).

Mice were monitored daily and tumor growth was measured at least 3 times per week with a digital caliper using the following formula: volume=length×width²×0.5. Responses were defined as complete remission (CR, no visible tumor) or partial remission (PR, at least 50% reduction of tumor volume). Animals were sacrificed when the tumor reached a volume>2000 mm³ or animals displayed signs of disease. All animal experiments were done under the project license "Tumor Targeting" issued to D. N. by the Kantonales Veterinäramt des Kantons Zürich (Bewilligung 198/2005).

Disseminated Lymphoma Xenograft Model

To model systemic disease, SCID mice were injected i.v. with 2×10⁶ Ramos lymphoma cells resuspended in 200 µL PBS. Dissemination and growth of B-cell lymphoma was allowed to occur for 8 days before the initiation of therapy. Mice were randomly divided into 6 groups (n≥6) and injected i.v. with either 20 µL19-IL2, 6.6 µg unconjugated rIL-2, or 200 µg rituximab (monotherapies), or 200 µg rituximab in combination with 20 µL19-IL2, 200 µg rituximab in combination with 6.6 µg unconjugated IL-2 (combination therapies), or saline on days 8, 11, 14, and 17 (Q3Dx4). Mice were monitored daily for the presence of hind-leg paralysis or signs of a deteriorating condition whereupon mice were sacrificed.

Onset of paralysis or death were set as end points and survival of mice was recorded for analysis of therapeutic efficacy. Animal experiments using the disseminated lymphoma model were done in accordance with amendment 1 to the project license "Tumor Targeting".

Statistical Analysis

Data are expressed as the mean±SE. Differences in tumor volume between different groups of mice were compared using the two-tailed Student's t test. Kaplan-Meier survival curves were performed to display therapeutic efficacy in the disseminated lymphoma model and comparisons were made using the log-rank test. Two-sided P values <0.05 were considered significant.

Results

In Vitro Localization: Immunohistochemistry on Xenograft Tumors

Immunohistochemical analyses on sections of Ramos lymphoma xenografts have been performed using L19 antibody specific to the EDB domain of fibronectin). As demonstrated in FIG. 1 (left panel), a specific staining of vascular structures in the lymphoma tissue could be observed for L19, reminiscent of its staining pattern in solid tumors, as exemplified with a human U87 glioblastoma xenograft (right panel). The pattern of EDB expression in lymphoma xenografts indicates that this isoform can serve as target for the selective delivery of bioactive compounds to the lymphoma site in vivo.

In Vivo Targeting Performance: Ex Vivo Fluorescence and Quantitative Biodistribution In the next step it was investigated whether EDB fibronectin expressed in lymphoma xenografts is accessible for the L19 antibody from the bloodstream in vivo. To this end, mice beating subcutaneous Ramos lymphoma tumors were injected i.v. with L19-SIP, chemically labeled with the fluorophore Cy3. After 24 h, animals were sacrificed and tumor sections were processed as described in Materials and Methods, FIG. 2a shows a 2-color fluorescence microscopic image of a lymphoma section, confirming the antibody localization on tumor vascular structures.

In order to evaluate antibody deposition quantitatively, mice bearing s.c. implanted Ramos lymphoma xenografts were injected i.v. with radioiodinated preparations of L19-SIP. As depicted in FIG. 2b, L19 displayed an accumulation in the lymphoma tissue with absolute tumor uptake values of 4.7% ID/g 24 h after injection, but only moderate tumor-to-blood ratios of 2.1 at this time point (tumor-to-organ ratios ranging from 2.7 to 7.1). However, after 48 h, the antibody was cleared from normal organs more rapidly, resulting in increased tumor-to-blood (4.8) and tumor-to-organ ratios (up to 17.3) and demonstrating a specific accumulation and retention of the antibody at the tumor site.

Therapeutic Activity of Single-Agent L19-IL2 and Single-Agent Rituximab Against Localized Lymphoma Xenografts It has been shown previously that the antibody-cytokine fusion protein L19-IL2 exhibited potent anti-cancer activity in various models of solid tumors (Menrad et al. (Expert Opin Ther Targets. 2005; 9:491-500), Carnemolla et al. (Blood. 2002; 99:1659-1665)). To evaluate the monotherapeutic efficacy of L19-IL2 in B-cell lymphoma, SCID mice were injected s.c. with 1×10$^7$ Ramos cells. On day 8 after tumor cell implantation, when tumors had reached 50-100 mm$^3$ in size, mice (n≥4) were treated i.v. either with 20 μL19-IL2 (corresponding to 6.6 μg rIL-2), 6.6 μg unconjugated rIL-2, 200 μg rituximab, or saline (Q3Dx4). FIG. 3 demonstrates that single-agent L19-IL2 and single-agent rituximab substantially inhibited lymphoma growth as compared to control mice treated with saline (P=0.024 and P=0.004, respectively). By contrast, equimolar amounts of unconjugated rIL-2 did not exhibit any significant therapeutic effect (P=0.383), similar to what has been reported previously for animal models of solid cancers and demonstrating the contribution of the antibody-mediated vascular targeting of the cytokine to the therapeutic effect (L19-IL2 vs. IL-2: P=0.044). However, both L19-IL2 and rituximab only delayed tumor growth when used as monotherapy and all animals experienced progressive disease in this experiment. While the fusion protein L19-IL2 reproducibly inhibited lymphoma growth (P=0.031), equimolar amounts of naked L19 in SIP or IgG format were therapeutically inactive when administered alone or in combination with free rIL-2, further reinforcing the concept that the therapeutic activity of L19-IL2 relied on the targeted delivery of the cytokine at the lymphoma site (FIG. 7).

To provide information about treatment-associated toxicity, animal weights were measured at least 3 times per week. No evidence of toxicity was observed, as in none of the therapy groups mice lost more than 3% of body weight throughout the study period.

Therapeutic Activity of L19-IL2 and Rituximab in Combination Against Localized Lymphoma Xenografts A variety of ways to enhance the clinical efficacy of rituximab have been reported, including the administration of rIL-2 to potentiate ADCC-mediated killing of lymphoma cells (Cartron et al., Blood. 2004; 104:2635-2642). Thus, we asked whether a combination of vascular-targeted IL-2 and anti-CD20 therapy would be therapeutically more effective than either therapeutic approach alone and, in particular, whether the antibody-mediated accumulation of IL-2 in the lymphoma tissue would exceed the efficacy of a combination of the unconjugated cytokine and rituximab. To this end, a combination therapy experiment was conducted according to the following scheme (≥5 mice per group): 200 μg rituximab+2.2 μg unconjugated rIL-2 ("low dose"), 200 μg rituximab+6.6 μg unconjugated rIL-2 ("high dose"), 200 μg rituximab+6.6 μL19-IL2 ("low dose", corresponding to 2.2 μg rIL-2), 200 μg rituximab+20 μg L19-IL2 ("high dose", corresponding to 6.6 μg rIL-2), or control saline. In analogy to the monotherapy experiment, injections were started on day 8 after tumor cell inoculation when palpable s.c. xenografts have developed and repeated every third day for 4 injections in total.

As shown in FIG. 4, rituximab in combination with unconjugated rIL-2 caused significant tumor growth delay as compared to controls (rIL-2$_{low\ and\ high\ dose}$ vs. saline: P<0.001). High dose rIL-2 was slightly more effective in increasing the efficacy of rituximab than low dose rIL-2 (P=0.038), however, no tumor regressions have been observed and all tumors continued to grow. In contrast, the combination of rituximab with the L19-IL2 fusion protein displayed a strikingly higher anti-lymphoma activity and induced complete eradications of established Ramos lymphomas in 4 of 5 mice in the high dose L19-IL2 group (L19-IL2$_{high\ dose}$ vs. saline: P<0.00001), with 3 of 4 CRs (complete remissions) already being achieved after 3 injections. In fact, the immunocytokine was remarkably more potent than the corresponding equimolar amount of unconjugated rIL-2 in combination with rituximab (L19-IL2$_{high\ dose}$ vs. rIL-2$_{high\ dose}$: P<0.001). Notably, even L19-IL2 at the lowest dose level combined with rituximab still displayed an excellent therapeutic activity (L19-IL2$_{low\ dose}$ vs. saline: P<0.00001; L19-IL2$_{low\ dose}$ vs. rIL-2$_{low\ dose}$: P<0.00001), inducing CRs in 4 of 5 cases after 4 cycles of therapy, whereas even a three-fold higher dose of the non-targeted cytokine combined with rituximab was only able to retard tumor growth (L19-IL2$_{low\ dose}$ vs. rIL-2$_{high\ dose}$:

P<0.001). While animals having achieved a CR in the low dose L19-IL2 group eventually relapsed after remission duration of 21, 48, 50, and 81 days, respectively, all CRs in the higher dose L19-IL2 group were durable and all mice remained tumor-free for an observation period of one year. Two mice (one in the low dose and one in the high dose L19-IL2 group) did not achieve a CR but the tumor mass was reduced to less than 20 mm$^3$.

To investigate whether the therapeutic performance of L19-IL2, alone or in combination, could be reproduced in a second lymphoma model, SCID mice bearing localized DoHH-2 follicular lymphoma xenografts were treated with similar conditions as indicated above. In analogy to the Ramos model, L19-IL2 was effective as a single-agent in inhibiting lymphoma growth (P<0.0001), yet without inducing tumor regressions, while the sum of its components (naked L19 and rIL-2) in equivalent doses showed no significant therapeutic activity. When combined with rituximab, L19-IL2 reproducibly led to complete tumor eradications in all cases (5/5) with no evidence of relapse at day 41 and was significantly more effective than single-agent rituximab or the combination of rituximab and non-targeted rIL-2 (and naked L19) (P<0.01), even though ⅖ CRs had been observed in both groups.

The therapeutic activity of all agents used against localized Ramos and DoHH-2 xenografts in mono- and combination therapies is summarized in Table 3.

Importantly, the therapeutic performance of the combination therapy was not associated with additional toxicity. Mice did not exhibit significant loss of body weight at any time point during the treatment (<3%), indicating that also the combination therapy regimens were well tolerated.

TABLE 1

Activity of rIL-2, L19-IL2 and rituximab, alone and in combination, against localized lymphoma xenografts

| Treatment | PR | CR | Relapse after CR |
|---|---|---|---|
| Ramos | | | |
| Saline | 0/9 | 0/9 | — |
| rIL-2 (6.6 µg) | 0/4 | 0/4 | — |
| L19-IL2 (20 µg) | 0/4 | 0/4 | — |
| Rituximab (200 µg) | 0/4 | 0/4 | — |
| Rituximab (200 µg) + rIL-2 (2.2 µg) | 0/5 | 0/5 | — |
| Rituximab (200 µg) + rIL-2 (6.6 µg) | 0/5 | 0/5 | — |
| Rituximab (200 µg) + L19-IL2 (6.6 µg) | 1/5 | 4/5 | 4/4 |
| Rituximab (200 µg) + L19-IL2 (20 µg) | 1/5 | 4/5 | 0/4 |
| DoHH-2 | | | |
| Saline | 0/5 | 0/5 | — |
| rIL-2 (6.6 µg) [+SIP(L19)] | 0/5 | 0/5 | — |
| L19-IL2 (20 µg) | 0/5 | 0/5 | — |
| Rituximab (200 µg) | 2/5 | 2/5 | 1/2 |
| Rituximab (200 µg) + rIL-2 (6.6 µg) [+SIP(L19)] | 3/5 | 2/5 | 1/2 |
| Rituximab (200 µg) + L19-IL2 (20 µg) | 0/5 | 5/5 | 0/5 |

SCID mice bearing established subcutaneous Ramos or DoHH-2 lymphoma xenografts were treated with the indicated therapeutic regimens. Responses were defined as partial remission (PR, at least 50% reduction of tumor volume) or complete remission (CR, no visible or palpable tumor). Data indicate number responding/total number of treatment group.
— not applicable.

Therapeutic Activity in the Disseminated Lymphoma Model

Therapeutic activity of L19-IL2 as a single-agent and in combination with rituximab against disseminated lymphoma xenografts Advanced NHLs in humans commonly develop as disseminated disease. To investigate the activity of L19-IL2 against systemic lymphoma, we chose the disseminated SCID/Ramos lymphoma model. SCID mice inoculated i.v. with lymphoma cells regularly develop paralysis of the hindlegs, resulting from lymphoma manifestations in the spinal cord and indicating the terminal phase of the disease. In accordance to published observations, i.v. injection of Ramos cells resulted in the development of hind-leg paralysis by day 26 in all cases in a pilot experiment, indicating an engraftment rate of 100% (data not shown). As paralysis preceded death in every case, the appearance of hind-leg paralysis was set as end point for survival analyses. Treatment initiation was delayed for 8 days to ensure engraftment and outgrowth of lymphoma cells. Dosing and scheduling of agents were identical to the ones used in the localized Ramos lymphoma model, and the activities of both mono-(rIL-2, L19-IL2, rituximab) and combination therapies (rituximab plus rIL-2, rituximab plus L19-IL2) were evaluated simultaneously in this experiment.

The Kaplan-Meier survival curve is shown in FIG. 5. By day 25, all saline-treated control mice succumbed to disseminated disease with a median survival time of 24 days. The administration of unconjugated rIL-2 alone did not exhibit a significant therapeutic benefit (median survival 24 days; P=0.518, log-rank test). In contrast, the corresponding dose of single-agent L19-IL2 (20 µg) extended the median survival time to 29 days (P<0.010, compared to non-targeted rIL-2) and was equally efficient as rituximab in delaying the appearance of the disease compared to saline-treated controls (median survival 29 and 30 days, respectively, vs. 24 days; P<0.001 for both agents). In combination therapies, the addition of rIL-2 to rituximab delayed the appearance of the disease only slightly compared to rituximab alone, without reaching statistical significance (34 vs. 30 days; P=0.180). Notably, while all mice treated with single-agent therapies as well as all mice treated with the combination of rituximab and non-targeted rIL-2 eventually developed terminal paralysis, 6 of 6 mice receiving L19-IL2 and rituximab in combination survived more than 60 days without showing clinical manifestations of the disease. On day 62, one mouse had to be killed because of weight loss and ocular discharge due to infection, with no evidence of paralysis or lymphoma manifestations at necropsy. Two additional mice had to be sacrificed on day 73 and 79, respectively, due to lymphoma development in an axillary lymph node, yet without hind-leg paralysis. The three remaining mice were still disease-free 310 days after tumor cell inoculation.

Validation of Target Expression in Human Lymphoma Samples

Finally, immunohistochemical analyses confirmed the presence and vascular expression pattern of EDB fibronectin in human B-cell malignancies, including diffuse large B-cell and Burkitt lymphomas (FIG. 6).

REFERENCES

Coiffier B, Lepage E, Briere J, et al. CHOP chemotherapy plus rituximab compared with rituximab alone in elderly patients with diffuse large-B-cell lymphoma. N Engl J Med 2002; 346:235-242.

Marcus R, Imrie K, Belch A, et al. CVP chemotherapy plus rituximab compared with CVP as first-line treatment for advanced follicular lymphoma. Blood 2005; 105:1417-1423.

Hiddemann W, kneba M, Dreyling M, et al. Frontline therapy with rituximab added to the combination of cyclophosphamide, doxorubicin, vincristine, and prednisolone (CHOP) significantly improves the outcome for patients with advanced-stage follicular lymphoma compared with CHOP alone: results of a prospective randomized study of the German Low-Grade Lymphoma Study Group. Blood 2005; 106:3725-3732.

Coiffier B. Treatment of non-Hodgkin's lymphoma: a look over the past decade. Clin Lymphoma Myeloma 2006; 7:S7-13.

Gordan L N, Grow W B, Pusateri A, et al. Phase II trial of individualized rituximab dosing for patients with CD20-positive lymphoproliferative disorders. J Clin Oncol 2005; 23:1096-1102.

Hoechster H S, Weller E, Gascoyne R, et al. Maintenance rituximab after CVP results in superior clinical outcome in advanced follicular lymphoma (FL): results of the E1496 Phase III Trial from the Eastern Cooperative Oncology Group and the Cancer and Leukemia Group B (abstract). Blood 2005; 106: No 349.

Habermann T M, Weller E A, Morrison V A, et al. Rituximab-CHOP versus CHOP alone or with maintenance rituximab in older patients with diffus large B-cell lymphoma. J Clin Oncol 2006; 24:3121-3127.

Cragg M S, Gleannie M J. Antibody specificity controls in vivo effector mechanisms of anti-CD20 reagent. Blood 2004; 103:2738-2743.

Vugmeyster Y, Beyer J, Howell K, et al. Depletion of B cells by a humanized anti CD20 antibody PRO70769 in *Macaca fascicularis*. J Immunother 2005; 28:212-219.

Stein R, Qu Z, Chen S, et al. Characterization of a new humanized anti-CD20, IMMU-106, and its use in combination with the humanized abti-CD22 antibody, epratuzumab, for the therapy of non-Hodgkin's lymphoma. Clin Cancer Res 2004; 10:2868-2878.

Hagenbeek A, Plesner T, Johnson P et al. HuMax-CD20, a novel fully human anti-CD20 monoclonal antibody: results of a phase I/II trial in relapsed or refractory follicular non-Hodgkin's lymphoma (abstract). Blood 2005; 106: 4760a.

Weiner G J, Bowles J A, Link B K, et al. Anti-CD20 monoclonal antibody (mAb) with enhanced affinity for CD16 activates NK cells at lower concentrations and more effectively than rituximab (abstract). Blood 2005; 106:348a.

Umana P, Mossner E, Brueckner P, et al. Novel 3rd generation humanized type II CD20 antibody with glycoengineered Fc and modified elbow hinge for enhanced ADCC and superior apoptosis induction (abstract). Blood 2006; 108: 229a.

McLaughlin P, Grillo-Lopez A J, Link B K et al. Rituximab chimeric anti-CD20 monoclonal antibody therapy for relapsed indolent lymphoma: half of patients respond to a four-dose treatment program. J Clin Oncol 1998; 16:2825-2833.

Leonard J P, Coleman M, Ketas J C, et al. Phase I/II trial of epratuzumab (humanized anti-CD22 antibody) in indolent non-Hodgkin's lymphoma. J Clin Oncol 2003; 21:3051-3059.

Leonard J P, Coleman M, Ketas J C, et al. Combination antibody therapy with epratuzumab and rituximab in relapsed of refractory non-Hodgkin's lymphoma. J Clin Oncol 2005; 23:5044-5051.

Leonard J P, Friedbereg J, Younes A, et al. A phase I/II study of galiximab (an anti-CD80 monoclonal antibody) in combination with rituximab for relapsed or refractory follicular lymphoma. Ann Oncol 2007; 18:1216-1223.

Fayad L, Patel H, Verhoef G et al., Clinical activity of the immunoconjugate CMC-544 in B-cell malignancies: preliminary report of the expanded maximum tolerated dose (MTD) coghort of phase 1 study (abstract). Blood 2006; 108:2711a.

Czuczman M S, THall A, Witzig T E, et al. Phase I/II study of galiximab, an anti-CD80 monoclonal antibody, for relapsed or refractory, follicular lymphoma. J Clin Oncol 2005:23:4390-4398.

Advani R, Forero-Torres A, Furmann R R, et al. SGN-40 (anti-huCD40 mAb) monotherapy induces durable objective responses in patients with relapsed aggressive non-Hodgkins's lymphoma: evidence of antitumor activity from a phase I study (abstract) Blood 2006; 108:695a.

Sauer S, Hoffmann J, Menrad A, Dürkop H, Menssen H D. Expression of ED-B Fibronectin in Tissues from Human Hematologic Malignancies (abstract) Blood 2006; 108.

Assous N, Gossec L, Dieude P et al. Rituximab therapy in rheumatoid arthritis in daily practice. J. Rheumatol. 2008; 35:31-4.

Eisenbeis C F, Grainger A, Fischer B, Baiocchi R A, Carrodeguas L, Roychowdhury S, Chen L, Banks A L, Davis T, Young D, Kelbick N, Stephens J, Byrd J C, Grever M R, Caligiuri M A, Porcu P. Combination immunotherapy of B-cell non-Hodgkin's lymphoma with rituximab and interleukin-2: a preclinical and phase I study. Clin. Cancer Res 2004; 10: 6101-6110;

W. L. Gluck, D. Hurst, A. Yuen, A. M. Levine, M. A. Dayton, J. P. Gockerman, J. Lucas, K. Denis-Mize, B. Tong, D. Navis, et al. Phase I Studies of Interleukin (IL)-2 and Rituximab in B-Cell Non-Hodgkin's Lymphoma: IL-2 Mediated Natural Killer Cell Expansion Correlations with Clinical Response Clin. Cancer Res, 2004; 10: 2253-2264

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding EP application No. 08075044.1, filed Jan. 17, 2008, and U.S. Provisional Application Ser. No. 61/021,718, filed Jan. 17, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A combination comprising at least
   (i) a fusion protein comprising two parts, wherein the first part is an antibody which specifically recognizes an extra domain B ($ED_b$) of fibronectin, and the second part is an Interleukin-2 polypeptide which comprises the amino acid sequence set forth in SEQ ID NO: 4; and
   (ii) rituximab.

2. A combination according to claim 1, wherein the antibody and the Interleukin-2 of said fusion protein are linked by a fusion protein linker.

3. A combination according to claim 1, wherein the antibody of (i) recognizes the $ED_b$ domain of fibronectin and specifically binds thereto with sub-nanomolar or nanomolar affinity.

4. A combination according to claim 1, wherein the antibody comprises complementarity determining region (CDR) sequences comprising VH-CDR1-3 sequences and VL-CDR1-3 sequences of the L19 antibody.

5. A combination according to claim 4, wherein
   the VH-CDR1-3 sequences are set forth in SEQ ID NO:6, SEQ ID NO:8 and SEQ ID NO:7, respectively; and
   the VL-CDR1-3 sequences are set forth in SEQ ID NO:9, SEQ ID NO:10 and SEQ ID NO:11.

6. A combination according to claim 1, wherein the antibody comprises at least one Variable heavy (VH) chain according to SEQ ID NO: 1 or at least one Variable light (VL) chain according to SEQ ID NO: 2.

7. A combination according to claim 1, wherein the antibody comprises one VH (variable heavy) chain according to SEQ ID NO: 1 and one VL (variable light) chain according to SEQ ID NO: 2.

8. A combination according to claim 1, wherein the antibody comprises at least one Variable heavy (VH) chain according to SEQ ID NO: 1 and at least one Variable light (VL) chain according to SEQ ID NO: 2, wherein the variable heavy chain and the variable light chain are connected by an antibody linker.

9. A combination according to claim 8, wherein the antibody linker is a polypeptide comprising at least 90% sequence identity to the polypeptide sequence set forth in SEQ ID NO: 3.

10. A combination according to claim 1, wherein the antibody and the Interleukin-2 are connected by a fusion protein linker.

11. A combination according to claim 10, wherein the fusion protein linker has a length of 1 to 30 amino acids.

12. A combination according to claim 10, wherein the fusion protein linker comprises the sequence set forth in SEQ ID NO: 5.

13. A pharmaceutical composition which comprises a combination according to claim 1 and a carrier.

14. A method for the treatment of lymphoma in a subject in need thereof, comprising administering into said subject, the combination according to claim 1.

15. A method according to claim 14, wherein the lymphoma is a B-cell lymphoma.

16. A method according to claim 15, wherein the B-cell lymphoma is non-Hodgkin's lymphoma.

17. A method for the treatment of an autoimmune disease in a subject in need thereof, comprising administering into said subject, the combination according to claim 1.

18. A method according to claim 17, wherein the autoimmune disease is rheumatoid arthritis, Crohn's disease, colitis ulcerosa or autoimmune hemolytic anemia.

\* \* \* \* \*